United States Patent
Dibas et al.

(10) Patent No.: US 9,095,576 B2
(45) Date of Patent: Aug. 4, 2015

(54) PHARMACEUTICAL COMPOSITIONS COMPRISING 4-[1-(2,3-DIMETHYLPHENYL)ETHYL]-3H-IMIDAZOLE DERIVATIVES FOR TREATING RETINAL DISEASES

(71) Applicant: Allergan, Inc., Irvine, CA (US)

(72) Inventors: Mohammed I. Dibas, Laguna Niguel, CA (US); John E. Donello, Dana Point, CA (US); Daniel W. Gil, Corona Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/680,730

(22) Filed: Nov. 19, 2012

(65) Prior Publication Data

US 2013/0131133 A1 May 23, 2013

Related U.S. Application Data

(60) Provisional application No. 61/562,112, filed on Nov. 21, 2011.

(51) Int. Cl.
*A01N 43/58* (2006.01)
*A01N 43/60* (2006.01)
*A61K 31/50* (2006.01)
*A61K 31/495* (2006.01)
*A61K 31/4174* (2006.01)

(52) U.S. Cl.
CPC ................................ *A61K 31/4174* (2013.01)

(58) Field of Classification Search
None
See application file for complete search history.

(56) References Cited

U.S. PATENT DOCUMENTS

| | | | |
|---|---|---|---|
| 5,474,979 A | 12/1995 | Ding | |
| 5,994,384 A * | 11/1999 | Åkerman et al. | 514/397 |
| 6,582,718 B2 | 6/2003 | Kawashima | |
| 7,297,679 B2 | 11/2007 | Chang | |
| 7,491,383 B2 | 2/2009 | Woodward | |
| 7,931,909 B2 | 4/2011 | Hughes | |
| 2005/0059583 A1 | 3/2005 | Acheampong | |
| 2005/0277584 A1 | 12/2005 | Tien | |
| 2007/0015691 A1 | 1/2007 | Chang | |
| 2007/0203144 A1* | 8/2007 | Kusari et al. | 514/249 |
| 2010/0022574 A1* | 1/2010 | Gulati | 514/282 |

FOREIGN PATENT DOCUMENTS

| | | |
|---|---|---|
| WO | 2007-084473 | 7/2007 |
| WO | 2010-093930 | 8/2010 |
| WO | WO 2010093930 A1 * | 8/2010 |

OTHER PUBLICATIONS

Fong et al., "Diabetic Retinopathy," Diabetes Care, vol. 26, Supplement 1, Jan. 2003.*
PubMed Retinal Vein Occlusion Central retinal vein occlusion; Branch retinal vein occlusion; CRVO; BRVO, http://www.ncbi.nlm.nih.gov/pubmedhealth/PMH0004583/ (evidentiary article) last reviewed Jun. 2, 2012.*
Pierce V. Kavanagh, Synthesis of Possible Metabolites of Medetomidine {1-(2,3-Dimethylphenyl)-1-[imidazol-4(5)-yl]ethane}, J. Chem. Research, 1993, 152-153, 4, US.
Salonen, Jarmo, Biotransformation of Medetomidine in the Rat, Xenobiotica, 1990, 471-480., 20(5), US.
Stahl, Heinrich et al, Handbook of Pharmaceutical Salts, Verlag Helvetica Chimica Acta—Zurich, 2002, 329-345.
Stoilov, Ivan, Synthesis of Detomidine and Medetomidine Metabolites: 1,2,3-Trisubstituted Arenes With 4'(5')-Imidazolylmethyl Groups, J. Heterocyclic Chem., 1993, 1645-1651, 30, US.
Y.-H. Hui, Analytical Method Development for the Simultaneous Quantitation of Dexmedetomidine and Three Potential Metabolites in Plasma, Journal of Chromatography, 1997, 281-291, 762, Elsevier, US.
Patent Cooperation Treaty, Notification of Transmittal of the International Search Report and the Written Opinion of the International Searching Authority, or the Declaration, Form PCT/ISA/220, Int. App. No. PCT/US2012/065942, Nov. 19, 2012.

* cited by examiner

*Primary Examiner* — Craig Ricci
*Assistant Examiner* — Jared D Barsky
(74) *Attorney, Agent, or Firm* — Barbara C. Potts

(57) ABSTRACT

The present invention relates to pharmaceutical compositions, containing 4-[1-(2,3-dimethylphenyl)ethyl]-1H-imidazole, (S) 4-[1-(2,3-dimethylphenyl)ethyl]-1H-imidazole or (S) [3-(1-(1H-imidazol-4-yl)ethyl)-2-methylphenyl]methanol, their use as pharmaceuticals for the treatment of retinal diseases, for retinal neuroprotection and vision enhancement.

1 Claim, 1 Drawing Sheet

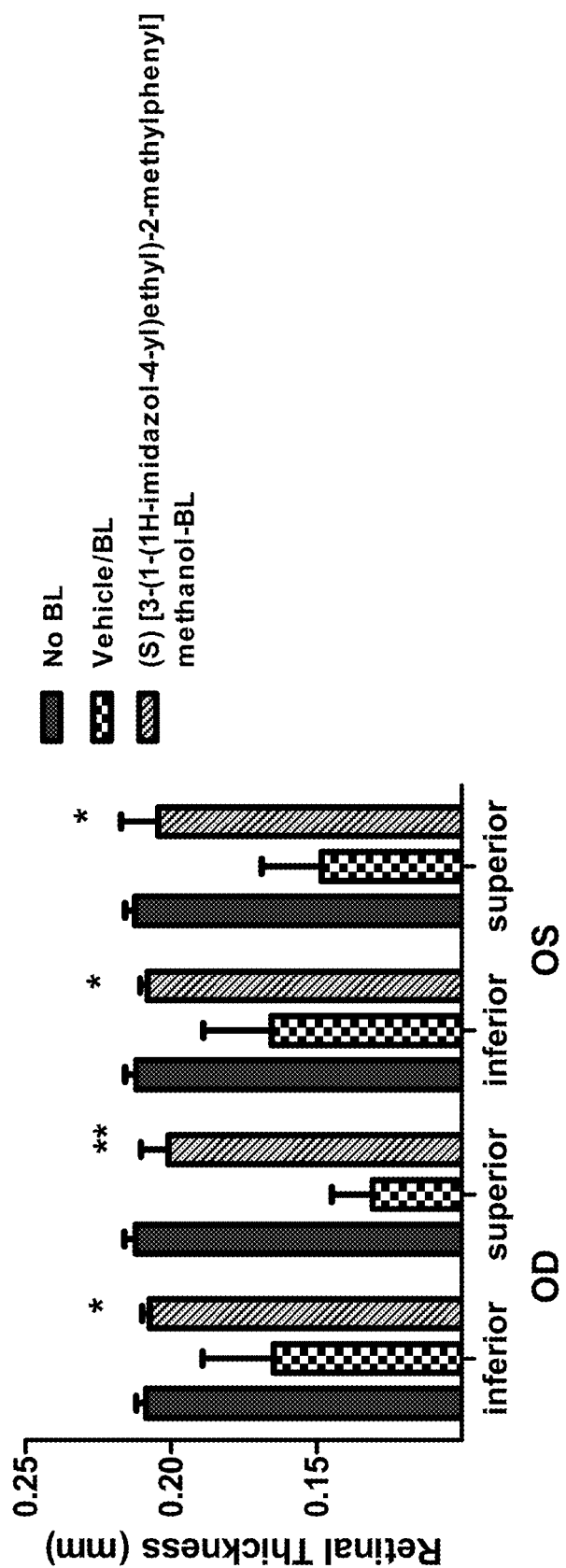

PHARMACEUTICAL COMPOSITIONS COMPRISING 4-[1-(2,3-DIMETHYLPHENYL)ETHYL]-3H-IMIDAZOLE DERIVATIVES FOR TREATING RETINAL DISEASES

RELATED APPLICATION

This application claims the benefit of U.S. Provisional Application Ser. No. 61/562,112, filed Nov. 21, 2011, the disclosure of which is hereby incorporated in its entirety herein by reference.

BACKGROUND OF THE INVENTION

1. Field of the Invention

The present invention relates to pharmaceutical compositions, containing 4-[1-(2,3-dimethylphenyl)ethyl]-1H-imidazole, (S) 4-[1-(2,3-dimethylphenyl)ethyl]-1H-imidazole or (S) [3-(1-(1H-imidazol-4-yl)ethyl)-2-methylphenyl]methanol, their use as pharmaceuticals for the treatment of retinal diseases, for retinal neuroprotection and vision enhancement. Three alpha-1 and three alpha-2 adrenergic receptors have been characterized by molecular and pharmacological methods. Activation of these alpha receptors evokes physiological responses with useful therapeutic actions.

2. Summary of the Related Art

Compound, 4-[1-(2,3-dimethylphenyl)ethyl]-1H-imidazole, generically known as, medetomidine is an alpha 2 adrenergic agonist, for use in the sedation of animals. The (S) enantiomer of medetomidine, generically known as dexmedetomidine, (S) 4-[1-(2,3-dimethylphenyl)ethyl]-1H-imidazole, is also indicated for use as a sedative or analgesic in cats and dogs administered as the hydrochloride salt. The metabolite of dexmedetomidine is (S) [3-(1-(1H-imidazol-4-yl)ethyl)-2-methylphenyl]methanol, generically known as, OH-dexmedetomidine, is a potent pan alpha2-adrenergic agonist, activating all three alpha2 receptor subtypes. These properties are beneficial for sustained activity, particularly when the drug is delivered continuously.

Dexmedetomidine is a potent alpha2-adrenergic agonist, activating all three alpha2 receptor subtypes. It is, however, a partial agonist of the alpha2A receptor, which may result in less receptor desensitization and down regulation (shown in Table 2). It is also highly selective for the alpha2 receptor relative to alpha1-adrenergic receptor activation. The compound (5-bromo-quinoxalin-6-yl)-imidazolidin-2-ylidene-amine (structure shown below) is generically known as brimonidine tartrate and is sold under the trademark ALPHAGAN®P (available from Allergan, Inc.). Pharmacological activation of the alpha 2 adrenergic receptor by brimonidine is a well established treatment for various visual disorders of the eye.

The metabolite of dexmedetomidine is (S) [3-(1-(1H-imidazol-4-yl)ethyl)-2-methylphenyl]methanol together with its racemic mixture, compound [3-(1-(1H-imidazol-4-yl)ethyl)-2-methylphenyl]methanol, are described in the literature in *Journal of Chromatography*, (1997), 762(1+2), 281-291 by Hui, Y.-H et al.

[3-(1-(1H-imidazol-4-yl)ethyl)-2-methylphenyl]methanol is described in "Synthesis of detomidine and medetomidine metabolites: 1,2,3-trisubstituted arenes with 4'(5')-imidazolylmethyl groups" in *Journal of Heterocyclic Chemistry* (1993), 30(6), (1645-1651) by Stoilov et al.

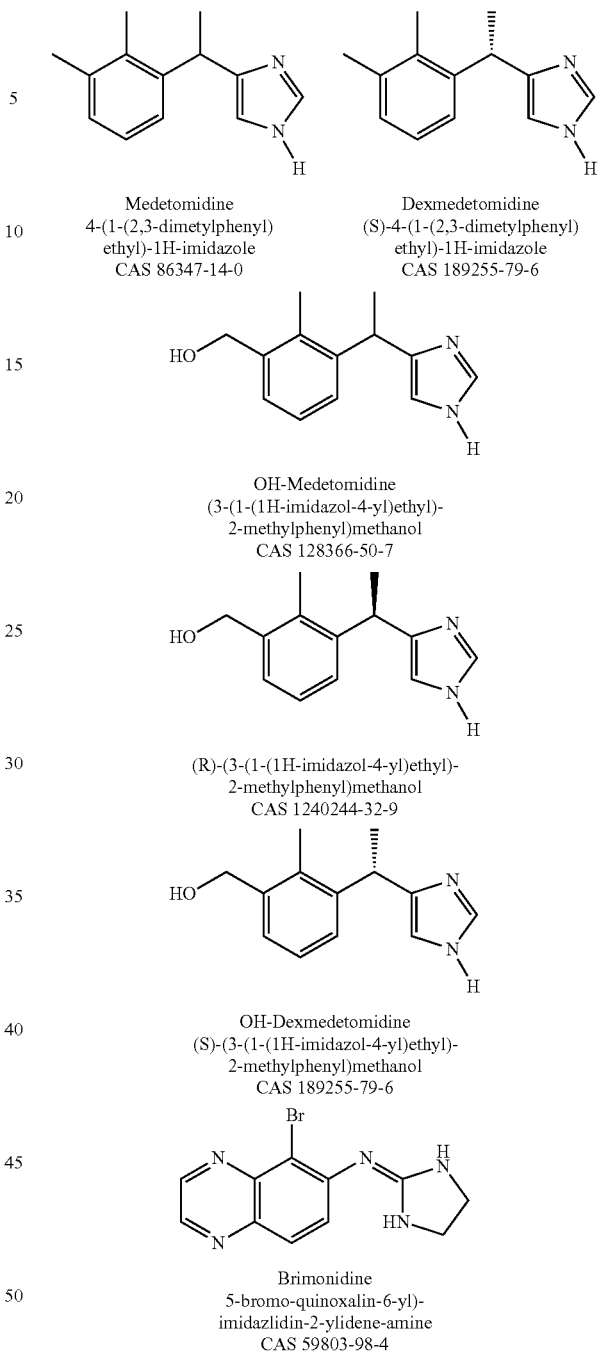

Medetomidine
4-(1-(2,3-dimetylphenyl)
ethyl)-1H-imidazole
CAS 86347-14-0

Dexmedetomidine
(S)-4-(1-(2,3-dimetylphenyl)
ethyl)-1H-imidazole
CAS 189255-79-6

OH-Medetomidine
(3-(1-(1H-imidazol-4-yl)ethyl)-
2-methylphenyl)methanol
CAS 128366-50-7

(R)-(3-(1-(1H-imidazol-4-yl)ethyl)-
2-methylphenyl)methanol
CAS 1240244-32-9

OH-Dexmedetomidine
(S)-(3-(1-(1H-imidazol-4-yl)ethyl)-
2-methylphenyl)methanol
CAS 189255-79-6

Brimonidine
5-bromo-quinoxalin-6-yl)-
imidazlidin-2-ylidene-amine
CAS 59803-98-4

Kavanagh, et al. describe [3-(1-(1H-imidazol-4-yl)ethyl)-2-methylphenyl]methanol in "Synthesis of Possible Metabolites of Medetomidine {1-(2,3-dimethylphenyl)-1-[imidazol-4(5)-yl]ethane" in *Journal of Chemical Research, Synopses* (1993), (4), 152-3.

[3-(1-(1H-imidazol-4-yl)ethyl)-2-methylphenyl)methanol] is described by Salonen, et al. in "Biotransformation of Medetomidine in the Rat" in *Xenobiotica* (1990), 20(5), 471-80.

PCT Int. Appl. WO 2010093930 A1 discloses [3-(1-(1H-imidazol-4-yl)ethyl)-2-methylphenyl]methanol and its (S) and (R) enantiomers and their use for treating pain.

SUMMARY OF THE INVENTION

The present invention provides pharmaceutical compositions containing medetomidine, it's (S) enantiomer, dexmedetomidine, or its metabolite, OH-dexmedetomidine, for treating retinal diseases including but not limited to: age related macular degeneration, wet macular degeneration, dry macular degeneration, geographic atrophy, diabetic retinopathy, diabetic macular edema and retinal vein occlusion. Our compounds of interest are also useful for enhancing vision in patients with vision loss from conditions including ocular hypertension, glaucoma, retinitis pigmentosa, nyctalopia, and neuritis secondary to multiple sclerosis.

BRIEF DESCRIPTION OF THE DRAWINGS

FIG. 1 shows that (S) [3-(1-(1H-imidazol-4-yl)ethyl)-2-methylphenyl]methanol reduced the damage caused by blue light.

DETAILED DESCRIPTION OF THE INVENTION

The present invention relates to a method of treating retinal diseases in a subject in need of such treatment, which comprises administering a therapeutically effective amount of a composition comprising medetomidine, dexmedetomidine, or OH-dexmedetomidine as alpha-2 agonists with therapeutic utility.

In one aspect of the invention, there is provided a method for treating retinal diseases in a patient in need thereof which comprises, consists essentially of or consists of or consists of administering a therapeutically effective amount of a pharmaceutical composition comprising, consisting essentially of or consisting of a therapeutically effective amount of medetomidine, or the tautomers thereof, or pharmaceutically acceptable salts thereof.

In another aspect of the invention, there is provided a method for treating retinal diseases in a patient in need thereof which comprises, consists essentially of or consists of or consists of administering a therapeutically effective amount of a pharmaceutical composition comprising, consisting essentially of or consisting of a therapeutically effective amount of dexmedetomidine or the tautomers thereof, or pharmaceutically acceptable salts thereof.

In another aspect of the invention, there is provided a method for treating retinal diseases in a patient in need thereof which comprises, consists essentially of or consists of or consists of administering a therapeutically effective amount of a pharmaceutical composition comprising, consisting essentially of or consisting of a therapeutically effective amount of OH-dexmedetomidine or the tautomers thereof, or pharmaceutically acceptable salts thereof.

In another aspect of the invention, there is provided a method for treating retinal diseases including but not limited to: age related macular degeneration, wet macular degeneration, dry macular degeneration, geographic atrophy, diabetic retinopathy, diabetic macular edema, neuritis secondary to multiple sclerosis and retinal vein occlusion.

In another aspect of the invention there is provided a method of enhancing vision in patients with vision loss from conditions including ocular hypertension, glaucoma, macular degeneration, retinitis pigmentosa, nyctalopia and neuritis secondary to multiple sclerosis, which comprises, consists essentially of or consists of or consists of administering a therapeutically effective amount of a pharmaceutical composition comprising, consisting essentially of or consisting of a therapeutically effective amount of medetomidine, or the tautomers thereof, or pharmaceutically acceptable salts thereof.

Enhancing vision loss involves improving visual function such as contrast sensitivity, vision in low light and acuity without having an effect on the loss of retinal cells due to the retinal disease.

In another aspect of the invention there is provided a method of enhancing vision in patients with vision loss from conditions including ocular hypertension, glaucoma, macular degeneration, retinitis pigmentosa and neuritis secondary to multiple sclerosis, which comprises, consists essentially of or consists of or consists of administering a therapeutically effective amount of a pharmaceutical composition comprising, consisting essentially of or consisting of a therapeutically effective amount of dexmedetomidine, or the tautomers thereof, or pharmaceutically acceptable salts thereof.

In another aspect of the invention there is provided a method of enhancing vision in patients with vision loss from conditions including ocular hypertension, glaucoma, macular degeneration, retinitis pigmentosa and neuritis secondary to multiple sclerosis, which comprises, consists essentially of or consists of or consists of administering a therapeutically effective amount of a pharmaceutical composition comprising, consisting essentially of or consisting of a therapeutically effective amount of OH-dexmedetomidine, or the tautomers thereof, or pharmaceutically acceptable salts thereof.

In another aspect of the invention, there is provided a method for treating retinal diseases wherein the pharmaceutical composition comprising, consisting essentially of or consisting of a therapeutically effective amount medetomidine, is selected from topical ocular application, direct injection, applications and formulations that may further enhance the long duration of actions such as a slow releasing pellet, suspension, gel, solution, cream, ointment, foams, emulsions, microemulsions, serums, aerosols, sprays, dispersions, microcapsules, vesicles, microparticles, ocular implant.

In another aspect of the invention, there is provided a method for treating retinal diseases wherein the pharmaceutical composition comprising, consisting essentially of or consisting of a therapeutically effective amount dexmedetomidine, is selected from topical ocular application, direct injection, applications and formulations that may further enhance the long duration of actions such as a slow releasing pellet, suspension, gel, solution, cream, ointment, foams, emulsions, microemulsions, serums, aerosols, sprays, dispersions, microcapsules, vesicles, microparticles, ocular implant.

In another aspect of the invention, there is provided a method for treating retinal diseases wherein the pharmaceutical composition comprising, consisting essentially of or consisting of a therapeutically effective amount OH-dexmedetomidine, is selected from topical ocular application, direct injection, applications and formulations that may further enhance the long duration of actions such as a slow releasing pellet, suspension, gel, solution, cream, ointment, foams, emulsions, microemulsions, serums, aerosols, sprays, dispersions, microcapsules, vesicles, microparticles, ocular implant.

As used herein, "tautomer" refers to the migration of protons between adjacent single and double bonds. The tautomerization process is reversible. Compounds described herein can undergo any possible tautomerization that is within the physical characteristics of the compound. The following is a tautomerization example that can occur in compounds described herein:

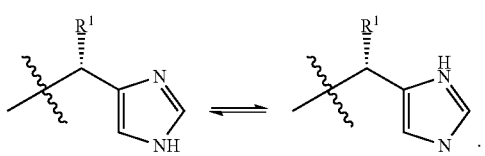

Compounds according to the present invention may exist in different polymorphic forms. Although not explicitly indicated in the above formula, such forms are intended to be included within the scope of the present invention.

"Vision loss", as used here, means deficits in vision field, contrast sensitivity, night vision, color vision, acuity.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds medetomidine, dexmedetomidine, or OH-dexmedetomidine are able to form.

The acid addition salt form of a compound such as: medetomidine, dexmedetomidine, or OH-dexmedetomidine, that occurs in its free form as a base can be obtained by treating the free base with an appropriate acid such as an inorganic acid, for example but not limited to hydrochloric acid, hydrobromic acid, sulfuric acid, phosphoric acid, nitric acid and the like; or an organic acid such as for example but not limited to, as citric acid, acetic acid, oxalic acid, tartaric acid, succinic acid, malic acid, fumaric acid, ascorbic acid, benzoic acid, tannic acid, pamoic acid, alginic acid, polyglutamic acid, naphthalene-sulfonic acid, naphthalenedisulfonic, and polygalacturonic acid as well as base addition salts such as those formed with alkali- and alkaline earth metals such as sodium, potassium and calcium and the like (Handbook of Pharmaceutical Salts, P. Heinrich Stahal & Camille G. Wermuth (Eds), Verlag Helvetica Chemica Acta-Zürich, 2002, 329-345).

The compounds of the invention, can also be administered as pharmaceutically acceptable quaternary salts known by those skilled in the art, which specifically include, but not limiting to the quaternary ammonium salt of the formula —NY$^+$Z$^-$, wherein Y is hydrogen, alkyl, or benzyl, and Z is a counterion, including but not limited to, chloride, bromide, iodide, —O-alkyl, toluenesulfonate, methylsulfonate, sulfonate, phosphate, or carboxylate (such as fumarate, benzoate, succinate, acetate, glycolate, maleate, malate, fumarate, citrate, tartrate, ascorbate, benzoate, cinnamoate, mandeloate, benzyloate, and diphenylacetate).

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include but are not limited to, glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The present invention concerns also the use of a compound: medetomidine, dexmedetomidine, or OH-dexmedetomidine or a pharmaceutically acceptable salt thereof, for the manufacture of a medicament for the therapeutic application. The present invention concerns also a method for manufacturing a medicament intended for therapeutic application wherein a compound: medetomidine, dexmedetomidine, or OH-dexmedetomidine or a pharmaceutically active derivative or salt thereof is used.

Since individual subjects may present a wide variation in severity of symptoms and each drug has its unique therapeutic characteristics, the precise mode of administration and dosage employed for each subject is left to the discretion of the practitioner. The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. The actual amount of the compound to be administered in any given case will be determined by a physician taking into account the relevant circumstances, such as the severity of the condition, the age and weight of the patient, the patient's general physical condition, the cause of the condition, and the route of administration. Additionally, the formulations may be designed to delay release of the active compound over a given period of time, or to carefully control the amount of drug released at a given time during the course of therapy.

Medetomidine, dexmedetomidine, or OH-dexmedetomidine and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. U.S. Pat. No. 7,931,909. Such biocompatible intraocular implants include medetomidine, dexmedetomidine, or OH-dexmedetomidine and a polymer associated with medetomidine, dexmedetomidine, or OH-dexmedetomidine to facilitate release thereof into an eye for an extended period of time.

Ophthalmic formulations of drug products are well known in the art and described in, for example, U.S. Patent Application Publication No. 20050059583; No. 20050277584; U.S. Pat. No. 7,297,679; and No. 20070015691; and U.S. Pat. Nos. 5,474,979 and 6,582,718. Medetomidine, dexmedetomidine, or OH-dexmedetomidine may be formulated with efficacy enhancing components as disclosed in U.S. Pat. No. 7,491, 383 B2.

With respect to the present invention reference to a compound or compounds, is intended to encompass that compound in each of its possible isomeric forms and mixtures thereof unless the particular isomeric form is referred to specifically.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following assays and animal models are used to demonstrate the potency and selectivity of the compounds according to the invention.

Results from an in vitro GTPase assay of alpha 2A receptor activation are shown in Table 1 for brimonidine, dexmedetomidine, OH-dexmedetomidine and OH-medetomidine (mixture of OH-dexmedetomidine and its opposite enantiomer). The data show that dexmedetomidine, OH-dexmedetomidine and OH-medetomidine are partial agonists with levels of efficacy 0.78, 0.65 and 0.26, respectively, of the efficacy of the full agonist brimonidine.

TABLE 1

| Entry | Compound Name | EC50 (nM) | Relative Efficacy |
|---|---|---|---|
| 1 | dexmedetomidine | 4 | 0.78 |
| 2 | brimonidine | 3 | 1.0 |
| 3 | OH-dexmedetomidine | 45 | 0.65 |
| 4 | OH-medetomidine | 20 | 0.26 |

In the GTPase assay, receptor activation results in dissociation of GDP and binding of the nonhydrolyzable [$^{35}$S] GTPyS to receptor-coupled G-proteins. The extent of binding is a measure of receptor activation. Membranes were prepared from HEK cells transiently expressing the alpha 2A receptor and the three subunits of the $G_i$ G-protein. Membranes were thawed and resuspended using a Polytron disrupter in 4° C. membrane buffer and quantified via Bradford assay. The quantified protein was then added to reaction buffer [50 mM Tris-HCl, 100 mM NaCl, 5 mM $MgCl_2$, 1 mM DTT, 1 mM EDTA, 3 µM propranolol, and 0.1 mM AMP; pH 7.4 and 4° C. to achieve a 100 µg/ml concentration, allowed to incubate for 15 minutes, and then incubated for an additional 10 minutes in the presence of 6 µM GDP. The above mixture was then aliquoted, 50 µL/well, in a 96 well plate, combined with an equal volume of test compound dissolved in assay buffer [50 mM Tris-HCl, 100 mM NaCl, 5 mM $MgCl_2$, 1 mM EDTA, and 1 mM DTT, pH 7.4 and 4° C.], and allowed to incubate for 5 minutes. Immediately following the above incubation, the mixture was combined with 50 µL of 1.5 nM [$^{35}$S]GTPyS in assay buffer and shaken covered for 60 minutes at 25° C. Assays were terminated by vacuum filtration over GF/B filters blocked with 0.5% BSA. Filters were then washed with 4° C. wash buffer [50 mM Tris-HCl, 100 mM NaCl, and 5 mM $MgCl_2$, pH 7.5. The incorporated [$^{35}$S] GTPyS was determined using a Microbeta 1450B liquid scintillation counter after the plates had dried overnight.

Binding studies showed that OH-Dexmedetomidine, a partial agonist induces very little down regulation of alpha 2A receptor. In contrast, brimonidine, a full agonist induced a strong reduction in the alpha 2A receptor density. Human embryonic kidney (HEK) 293T cells stably transfected with the α2A-adrenergic receptor were grown to 50-60% confluency on T-175 culture flasks in DMEM (Gibco, cat. #11995), 10% FBS (Gibco, cat. #16140), 0.25 µg/ml puromycin (Sigma, cat. # P-8833), and 1% antibiotic-antimycotic (Gibco, cat. #15240) maintained at 37° C. and 5% $CO_2$. After reaching the desired confluency, the cells were incubated for 24 hours in growth media treated with 0, 1,000, or 10,000 nM brimonidine and maintained at 37° C. and 5% $CO_2$. The cells were then washed with room temperature Dulbecco's phosphate buffered saline (DPBS; Gibco, cat. #14190).

TABLE 2

| Concentration | Percent of B max Decrease Compound | |
|---|---|---|
| (μM) | Brimonidine | OH-Dexmedetomidine |
| 1 | −45 | −25 |
| 10 | −60 | −14 |

Example 1

Membrane [Methyl-3H] Rauwolscine Saturation Binding

Cells were harvested with 4° C. Tris-EDTA buffer [50 mM Tris-HCl, 5 mM EDTA; pH 7.4] and centrifuged at 5,000×g for 5 minutes at 4° C. Membrane preparation was conducted by resuspending the cell pellets in 4° C. Tris-EDTA buffer and lysed with a Polytron disrupter two times (setting 7, 5 seconds each). The lysed suspension was then centrifuged at −35,000×g for 32 minutes at 4° C. After decanting the supernatant, the pelleted material was further lysed in 4° C. Tris buffer [50 mM Tris-HCl; pH 8.0] using the Polytron disrupter (setting 4, 5 seconds). Membranes were then aliquoted, pelleted at −37,000×g for 32 minutes at 4° C., and stored at −80° C. until use.

Membranes were thawed and resuspended using a Polytron disrupter in 4° C. HBSS-HEPES buffer [1 part 1M HEPES: 5 parts 10× Hank's Balanced Salt Solution: 43.8 parts $H_2O$; pH 7.4 with KOH) and quantified via Bradford assay. The quantified protein was further diluted with HBSS-HEPES buffer to achieve a 100 μg/ml concentration. Membrane suspension was plated in a 96-well plate at 200 lμLs/weil±10 μM phentolamine HCl (Sigma, cat. # P-7547) and [Methyl-$^3$H] Rauwolscine (15 nM to 0.05 nM; PerkinElmer, cat. # NET722250UC). The assay plate was slowly shaken and incubated at 25° C. for ninety minutes. Immediately following the above incubation, the assays were terminated by vacuum filtration over GF/B filters. Filters were then washed with 4° C. HBSS-HEPES buffer. The incorporated [Methyl-$^3$H] Rauwolscine was determined using a Microbeta 1450B liquid scintillation counter after the plates had dried overnight.

Example 2

The Blue Light Model

In order to demonstrate the advantage of partial alpha 2A agonists in treatment of retinal disease, OH-dexmedetomidine was compared to the vehicle in the blue light model of retinal degeneration in rats. Drugs were administered continuously with subcutaneous infusion pumps at a dose of 1 mg/kg/day starting two days before blue light exposure. These concentrations result in drug levels in the retina of 2.3 ng/g OH-dexmedetomidine which are sufficient for pharmacological activity. Twenty 4-month old male Sprague Dawley rats (body weight 470-550 g) were used in this study. The animals were exposed to room light on a 12 hour light/12 hour dark cycle before the experiment. All animals were dark adapted overnight (16-20 hours) before blue light. Under the intensity of 6100-6500 lux, rats were exposed to blue light for 4 hours. After the blue light, rats were placed in the dark for another 3 days before returning to normal 12 hour light/12 hour dark. Ocular Coherence Tomography (OCT) measurement was performed at 7 days post blue light exposure. The results of FIG. 1 demonstrate that blue light exposure with just saline treatment leads to dramatic reduction of retinal thickness measured by OCT, particularly in the superior retina. Histology studies have shown that the reduction in retinal thickness is attributable to loss of photoreceptors. The treatment with OH-dexmedetomidine significantly reduced the damage caused by blue light.

What is claimed is:

1. A method of treating age related macular degeneration, wet macular degeneration, or dry macular degeneration, in a subject in need of such treatment, which comprises administering a pharmaceutical composition comprising a therapeutically effective amount of (S) [3-(1-(1H-imidazol-4-yl) ethyl)-2-methylphenyl] methanol, or a pharmaceutically acceptable salt thereof.

* * * * *